United States Patent
Bertsch

(10) Patent No.: US 11,864,724 B2
(45) Date of Patent: Jan. 9, 2024

(54) OCCLUSION DEVICE

(71) Applicant: Vitalitec International Inc., Plymouth, MA (US)

(72) Inventor: Karrie Bertsch, Los Gatos, CA (US)

(73) Assignee: VITALITEC INTERNATIONAL, INC., Plymouth, MA (US)

( * ) Notice: Subject to any disclaimer, the term of this patent is extended or adjusted under 35 U.S.C. 154(b) by 87 days.

(21) Appl. No.: 17/382,434

(22) Filed: Jul. 22, 2021

(65) Prior Publication Data

US 2023/0028480 A1 Jan. 26, 2023

(51) Int. Cl.
| | |
|---|---|
| A61B 17/128 | (2006.01) |
| A61B 34/30 | (2016.01) |
| A61B 17/122 | (2006.01) |
| A61B 17/00 | (2006.01) |
| A61B 17/12 | (2006.01) |

(52) U.S. Cl.
CPC ........ *A61B 17/1285* (2013.01); *A61B 17/122* (2013.01); *A61B 34/30* (2016.02); *A61B 2017/00367* (2013.01); *A61B 2017/12004* (2013.01)

(58) Field of Classification Search
CPC ... A61B 17/1285; A61B 17/122; A61B 17/29; A61B 17/11; A61B 34/30; A61B 2017/00367; A61B 2017/12004; A61B 2017/00252; A61B 2017/1107; A61B 2017/1135
See application file for complete search history.

(56) References Cited

U.S. PATENT DOCUMENTS

| | | |
|---|---|---|
| 5,618,307 A | 4/1997 | Donlon et al. |
| 6,620,177 B2 | 9/2003 | Buelna et al. |
| 8,080,023 B2 * | 12/2011 | Gold ............... A61B 17/11 606/213 |
| 2002/0116017 A1 | 8/2002 | Buelna et al. |
| 2005/0043758 A1 * | 2/2005 | Golden ............ A61B 10/06 606/205 |
| 2005/0222665 A1 | 10/2005 | Aranyi |
| 2011/0152895 A1 * | 6/2011 | Nyuli ............... A61B 17/122 606/151 |
| 2014/0017660 A1 * | 1/2014 | Steinman ......... A61B 17/28 435/1.2 |
| 2014/0166720 A1 | 6/2014 | Chowaniec et al. |
| 2016/0151056 A1 * | 6/2016 | Lederman ......... A61B 17/11 606/213 |
| 2018/0199985 A1 * | 7/2018 | Wang ............... A61B 18/085 |
| 2018/0256163 A1 | 9/2018 | Evans et al. |

FOREIGN PATENT DOCUMENTS

WO 2021/087461 A2 5/2021

OTHER PUBLICATIONS

Extended European Search Report dated Dec. 7, 2022 for corresponding application EP22186163.6.

* cited by examiner

*Primary Examiner* — Shaun L David
*Assistant Examiner* — Rachael L Geiger
(74) *Attorney, Agent, or Firm* — Bachman & LaPointe, P.C.

(57) ABSTRACT

An occlusion device includes an elongate shaft; a lower jaw extending from a distal end of the elongate shaft; an upper jaw pivotably mounted relative to the lower jaw; and a control member at a proximal end of the elongate shaft, the control member being operatively associated with the upper jaw to cause pivot of the upper jaw relative to the lower jaw. A method is also disclosed.

24 Claims, 15 Drawing Sheets

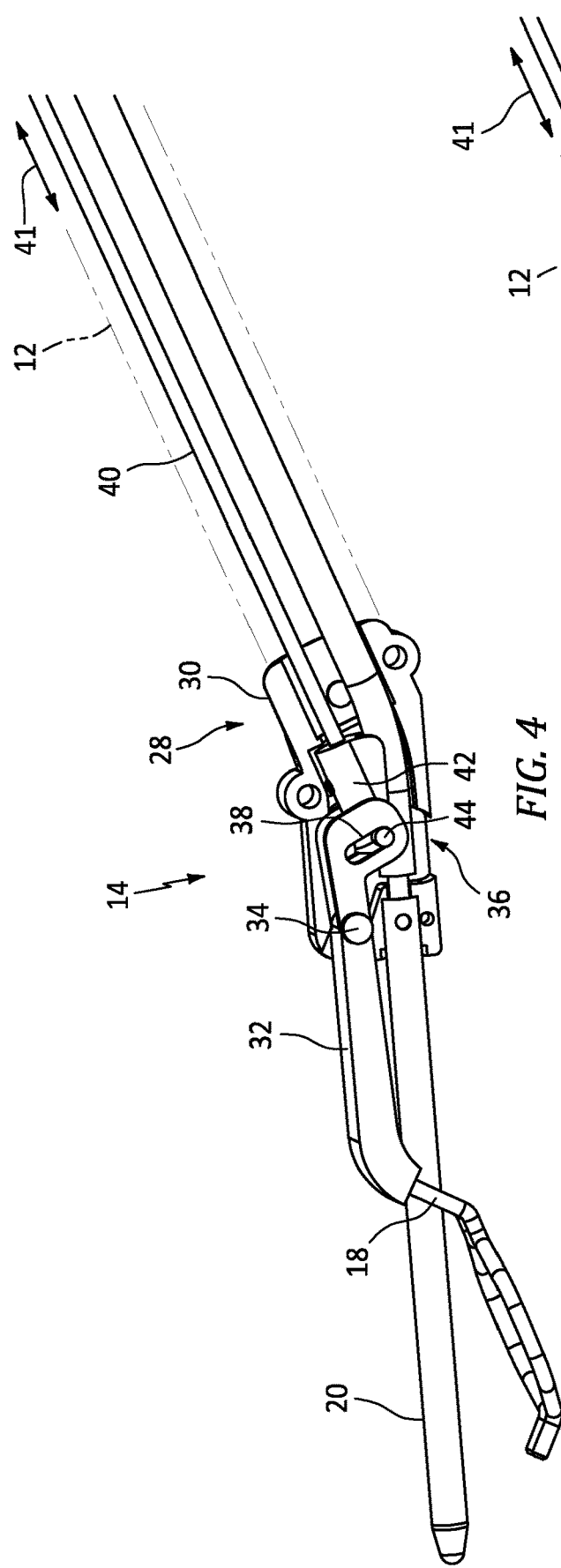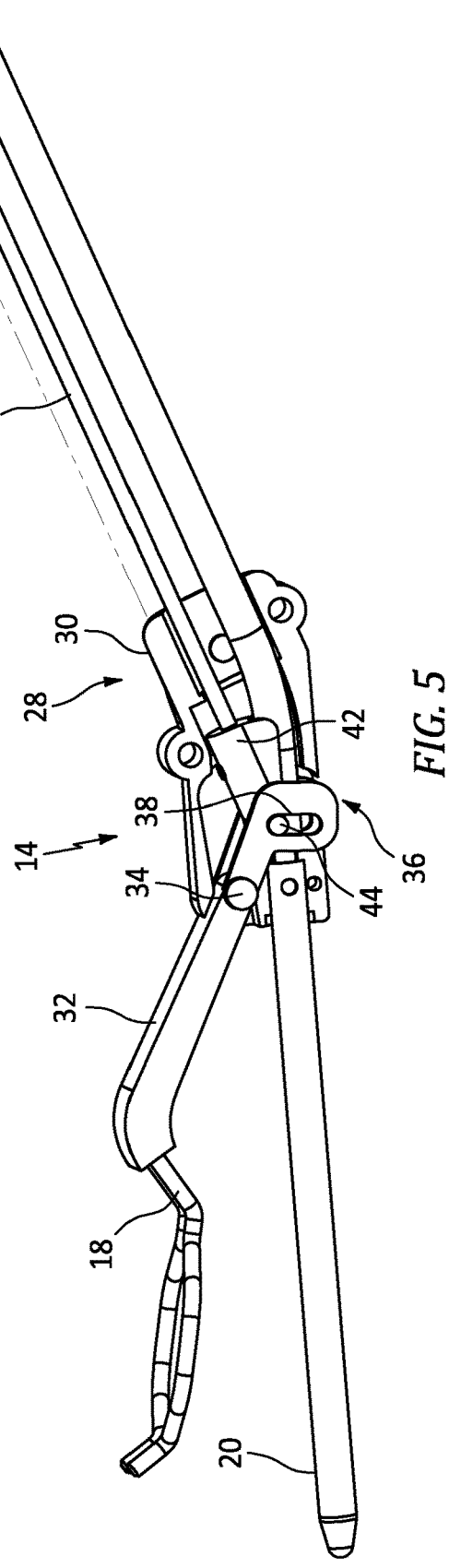

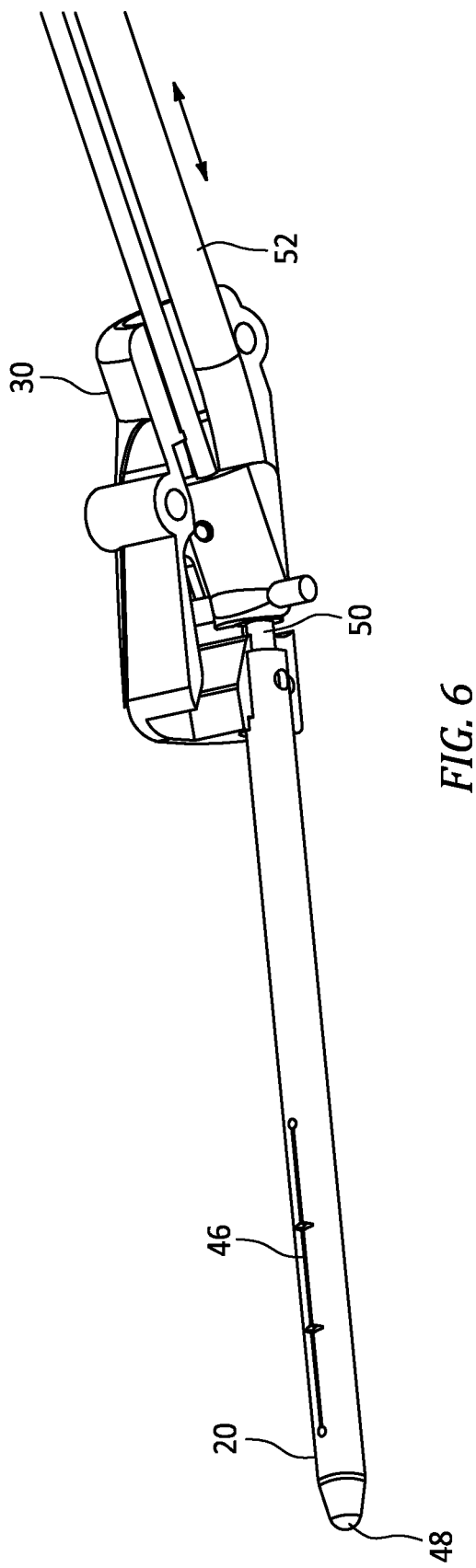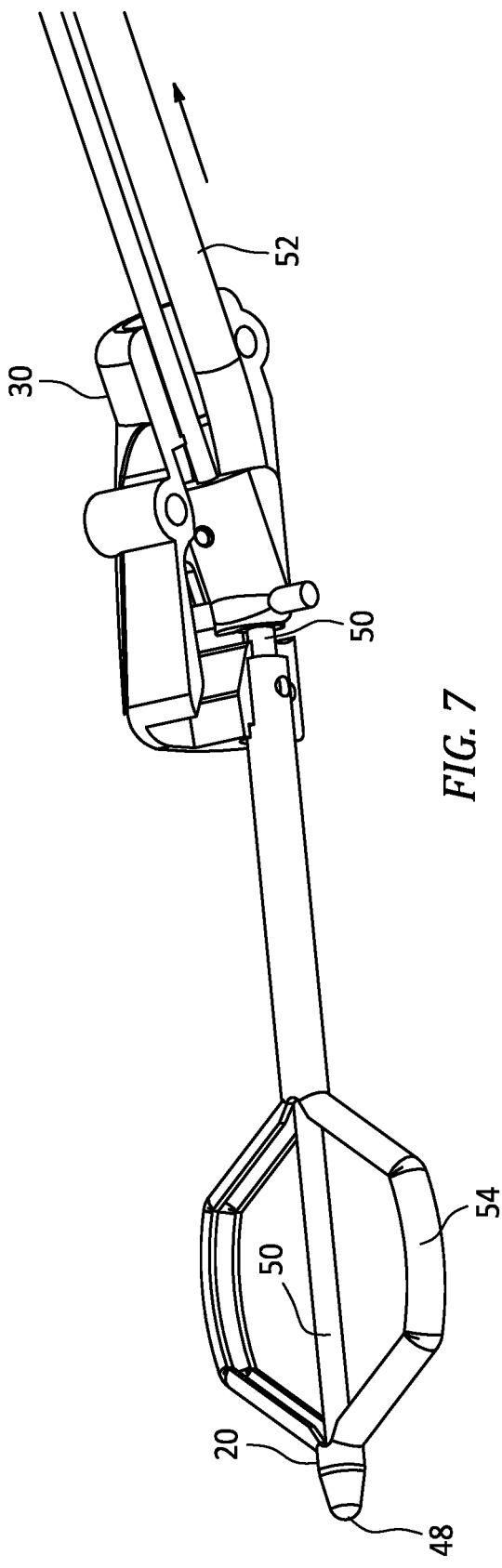

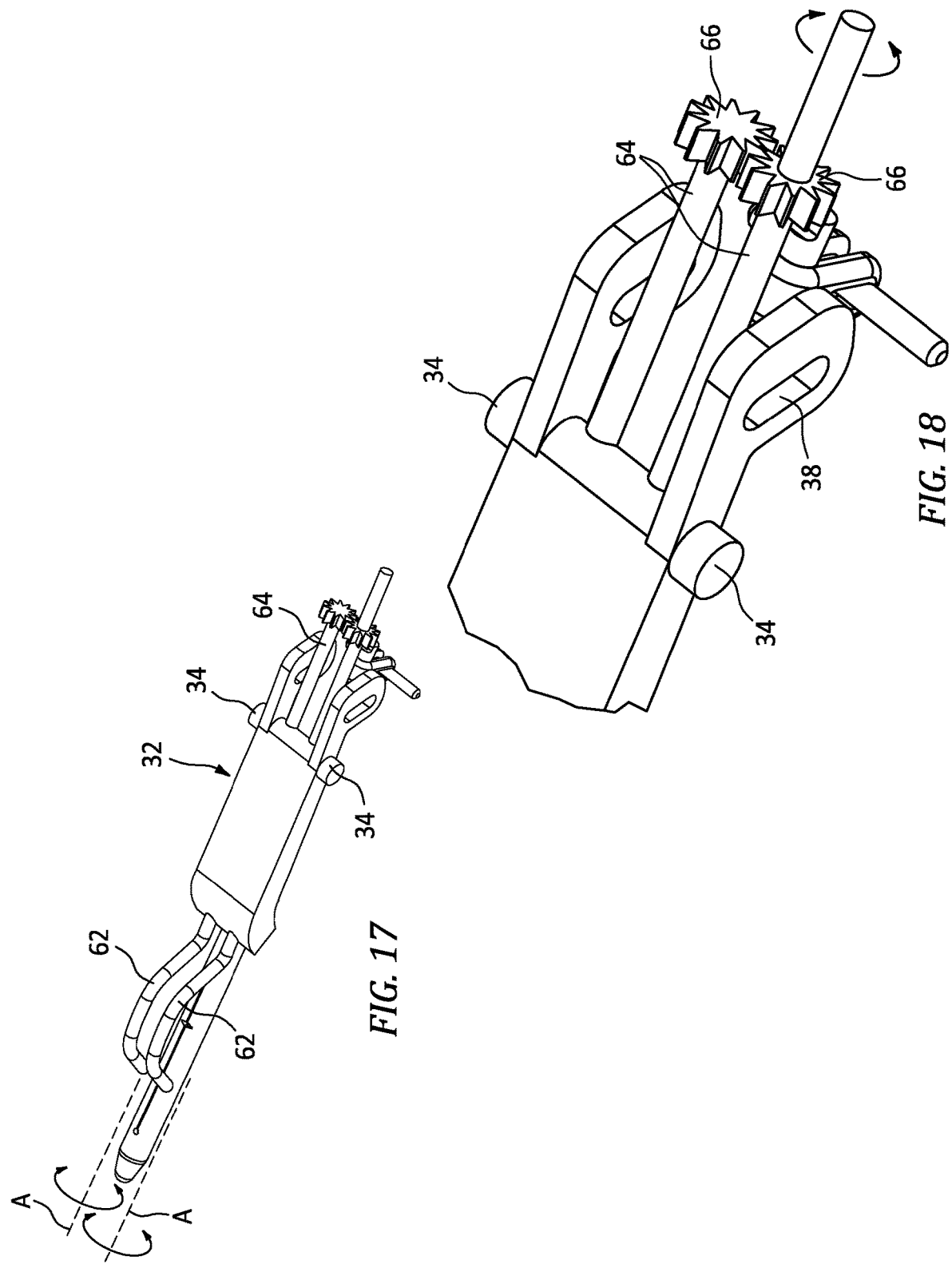

OCCLUSION DEVICE

BACKGROUND OF THE INVENTION

The invention relates to the fields of vascular and cardiovascular surgery, and more particularly to a device and method for obtaining hemostatic sealing when performing graft procedures especially in a minimally invasive setting.

Vascular and cardiovascular grafting procedures typically require the complete, or at least partial, occlusion of a selected vessel. For example, in the field of cardiovascular surgery, coronary artery bypass graft (CABG) procedures involving proximal anastomosis require the full, or at least partial, occlusion of the aorta. During proximal anastomosis, a vein or arterial graft is sewn to the aorta for revascularization of diseased or otherwise compromised coronary arteries. The internal mammary artery, saphenous vein and radial artery of the arm are examples of grafts used as bypass vessels. Occlusion of the aorta is typically accomplished by clamping. A variety of clamp configurations are in common use for full or partial occlusion procedures. For procedures involving cardiopulmonary bypass, full aortic occlusion is required, typically performed with a crossclamp. Partial occlusion is used in either on or off-pump coronary artery bypass graft procedures for proximal anastomosis. Occlusion of the aorta prevents blood flow from entering the graft target site, creating a bloodless field for the surgeon to then sew the graft to the aorta. Once the graft is sewn to the aorta, the surgeon removes the clamp, once again allowing blood flow through the anastomotic region.

One device for performing these occlusions is disclosed in U.S. Pat. No. 8,080,023, granted Dec. 20, 2011. This device performs well in creating a bloodless field. However, the configuration and dynamics of the device require significant entry to the occlusion site, and are not well suited for minimally invasive procedures. The present disclosure addresses this need.

SUMMARY OF THE INVENTION

The device as disclosed herein allows for reliable occlusion of a body part, for example establishing hemostasis prior to grafting procedures, with proximally located controls that greatly expand the functionality of the device.

According to this disclosure, an occlusion device, comprises an elongate shaft; a lower jaw extending from a distal end of the elongate shaft; an upper jaw pivotably mounted relative to the lower jaw; and a control member at a proximal end of the elongate shaft, the control member being operatively associated with the upper jaw to cause pivot of the upper jaw relative to the lower jaw.

In one non-limiting configuration, the lower jaw is laterally configurable between a withdrawn position and an expanded position, and wherein the upper jaw comprises a clamping member corresponding in shape to the lower jaw when the lower jaw is in the laterally expanded position.

In another non-limiting configuration, the upper jaw is laterally configurable between a withdrawn position and an expanded position, and wherein the expanded position of the upper jaw corresponds in shape to the expanded position of the lower jaw.

In a still another non-limiting configuration, the upper jaw comprises at least two components, and the at least two components move between the withdrawn position and the expanded position by rotating around a longitudinal axis of the upper jaw.

In a further non-limiting configuration, the at least two components have gears at proximal ends, and further comprising a rotation imparting member extending through the elongated shaft and rotatable from a proximal end of the elongated shaft to control position of the upper jaw between the withdrawn position and the expanded position.

In a still further non-limiting configuration, the device further comprises a housing at the distal end of the shaft, wherein the upper jaw is pivotably mounted to the housing.

In another non-limiting configuration, the device further comprises a linkage movable relative to the housing and connected to the upper jaw, and a pull rod axially movable along the elongate shaft and connected to the linkage, whereby axial movement of the pull rod moves the linkage and causes pivot of the upper jaw relative to the lower jaw.

In another non-limiting configuration, the device further comprises a pull tube mounted in the elongate shaft and extending into the housing for operating the lower jaw, and wherein the linkage slides along the pull tube when the linkage is moved within the housing.

In still another non-limiting configuration, the upper jaw is mounted in a lever pivotably mounted to the housing at a point of the lever, and having a proximal head that is connected to the linkage.

In a further non-limiting configuration, the proximal head is angled relative to the body of the lever and has a slot, and wherein the linkage has a post slidably engaged in the slot.

In a still further non-limiting configuration, a pull rod is axially movable along the elongate shaft and pivotably connected to the upper jaw whereby axial movement of the pull rod causes pivot of the upper jaw relative to the lower jaw.

In another non-limiting configuration, the upper jaw comprises a lever mounted for pivot relative to the housing, and having a receptacle for pivotably receiving a distal head of the pull rod.

In still another non-limiting configuration, the receptacle has a proximally facing slot, and the pull rod passes through the proximally facing slot.

In a further non-limiting configuration, the lower jaw comprises a flexible member having an axial slit, and further comprising a control rod slidable in the lower jaw and connected to a distal end of the lower jaw whereby proximal movement of the control rod pulls the distal end of the lower jaw proximally and moves the lower jaw to an expanded position.

In a still further non-limiting configuration, the device further comprises a pull tube slidably mounted in the elongate shaft and connected to the control rod for controlling the lower jaw.

In another non-limiting configuration, the lower jaw extends from the elongate shaft at an angle relative to the shaft of between 0 and 60 degrees.

In still another non-limiting configuration, the angle is between 0 and 45 degrees.

In a further non-limiting configuration, the angle is between 0 and 30 degrees.

In a still further non-limiting configuration, the shaft is flexible.

In another non-limiting configuration, the device further comprises a robot mechanism connect to the device and programmed to operate the control member.

In another embodiment of the disclosure, a method for occlusion of a body part, comprises the steps of accessing the body part with an occlusion device, comprising an elongate shaft; a lower jaw extending from a distal end of the elongate shaft; an upper jaw pivotably mounted relative to the lower jaw; and a control member at a proximal end of the elongate shaft, the control member being operatively associated with the upper jaw to cause pivot of the upper jaw relative to the lower jaw; positioning the occlusion device such that the body part is between the lower jaw and the upper jaw; and operating the control member to cause the upper jaw to pivot toward the lower jaw and occlude the body part between the lower jaw and the upper jaw.

In another non-limiting configuration, the lower jaw is laterally configurable between a withdrawn position and an expanded position, and wherein the upper jaw comprises a clamping member corresponding in shape to the lower jaw when the lower jaw is in the laterally expanded position; and further comprising the step of configuring the lower jaw to the withdrawn position during the accessing step, and configuring the lower jaw to the expanded position before the operating step.

In still another non-limiting configuration, the upper jaw is laterally configurable between a withdrawn position and an expanded position, and wherein the expanded position of the upper jaw corresponds in shape to the expanded position of the lower jaw, and further comprising the steps of configuring the upper jaw to the withdrawn position before during the accessing step, and configuring the upper jaw to the expanded position before the operating step.

In a further non-limiting configuration, the body part is a body part of a human aorta.

In a still further non-limiting configuration, the accessing step comprises entering the body through the abdominal wall and passing the lower jaw through the body part to an occlusion site on the body part.

In another non-limiting configuration, the method further comprises the step of, after occluding the body part, pivoting the shaft to a pivoted position.

In still another non-limiting configuration, the method is at least partially conducted by a robot mechanism.

The foregoing features and elements may be combined in various combinations without exclusivity, unless expressly indicated otherwise. These features and elements as well as the operation thereof will become more apparent in light of the following description and the accompanying drawings. It should be appreciated that the following description and drawings are intended to be exemplary in nature and non-limiting.

BRIEF DESCRIPTION OF THE DRAWINGS

A detailed description of non-limiting embodiments of the present disclosure follows, with reference to the attached drawings, wherein:

FIG. 4 is an internal view of the jaw assembly of the device of FIG. 1 with the upper jaw in a lower position;

FIG. 5 is an internal view of the jaw assembly of the device of FIG. 1 with the upper jaw in a lifted position;

FIG. 6 is an internal view of the jaw assembly of the device of FIG. 1 (without the upper jaw) with the lower jaw in a withdrawn or narrow profile position;

FIG. 7 is an internal view of the device of FIG. 1 (without the upper jaw) with the lower jaw in an expanded position;

FIG. 17 illustrates an alternative and non-limiting configuration of an upper jaw assembly wherein the upper jaw is also configurable between a withdrawn position and an expanded position;

FIG. 18 is an enlarged view of the structure of FIG. 17;

DETAILED DESCRIPTION

The invention relates to a device for use in occluding a body part, especially during vascular or cardiovascular surgery, and to a method for occlusion using the device.

Figure 1:
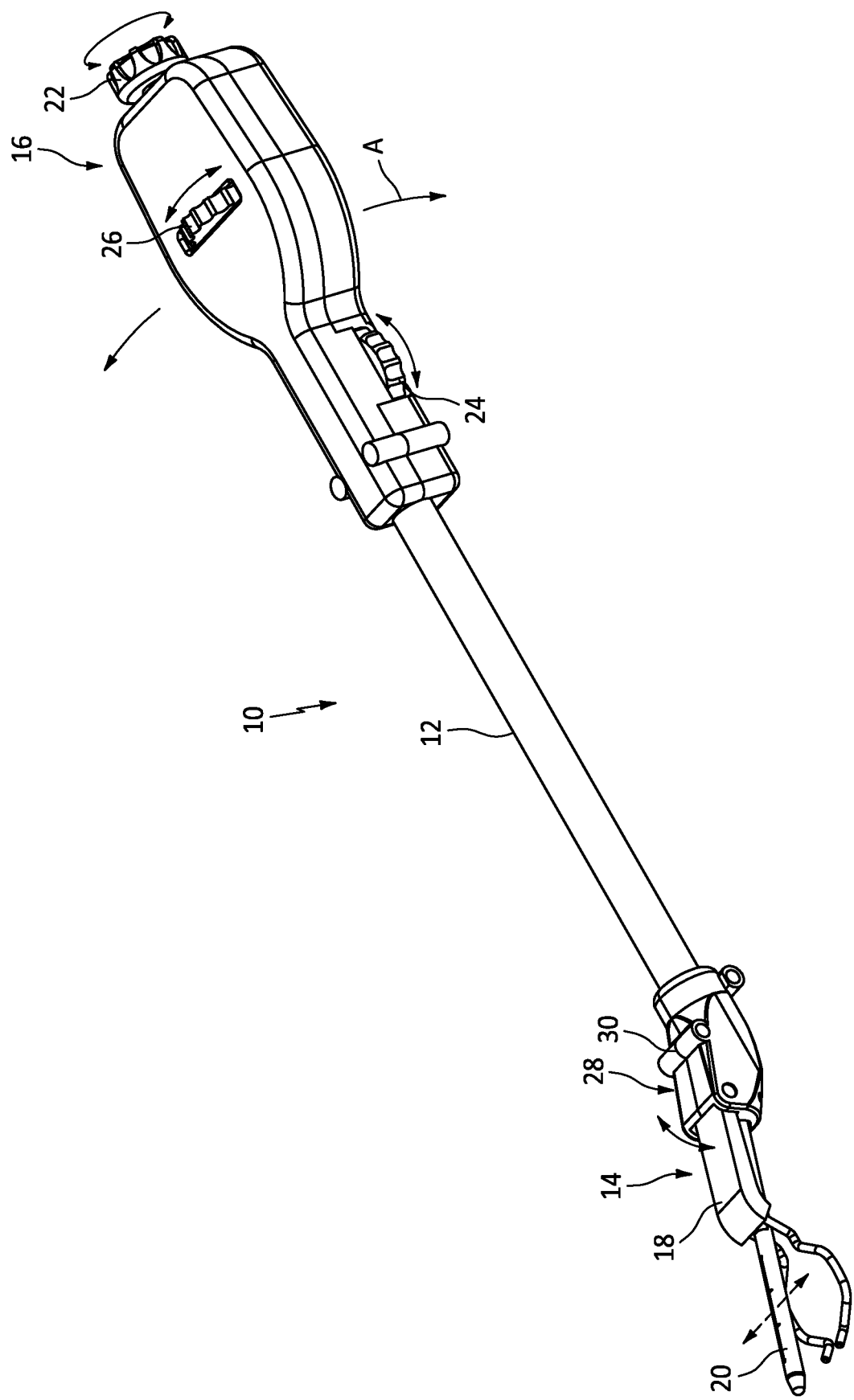
FIG. 1 is a perspective view of a non-limiting configuration of a minimally invasive occlusion device.

FIG. 1 shows a device 10 having an elongated shaft 12, a jaw assembly 14 at one end of the shaft 12, and a control housing or assembly 16 at the other end of shaft 12. The jaw assembly as disclosed herein will at times be referred to as being at the distal end of shaft 12, while control housing 16 will be referred to as being at the proximal end of shaft 12. Distal and proximal positions are considered with respect to the user of the device.

Figure 2:
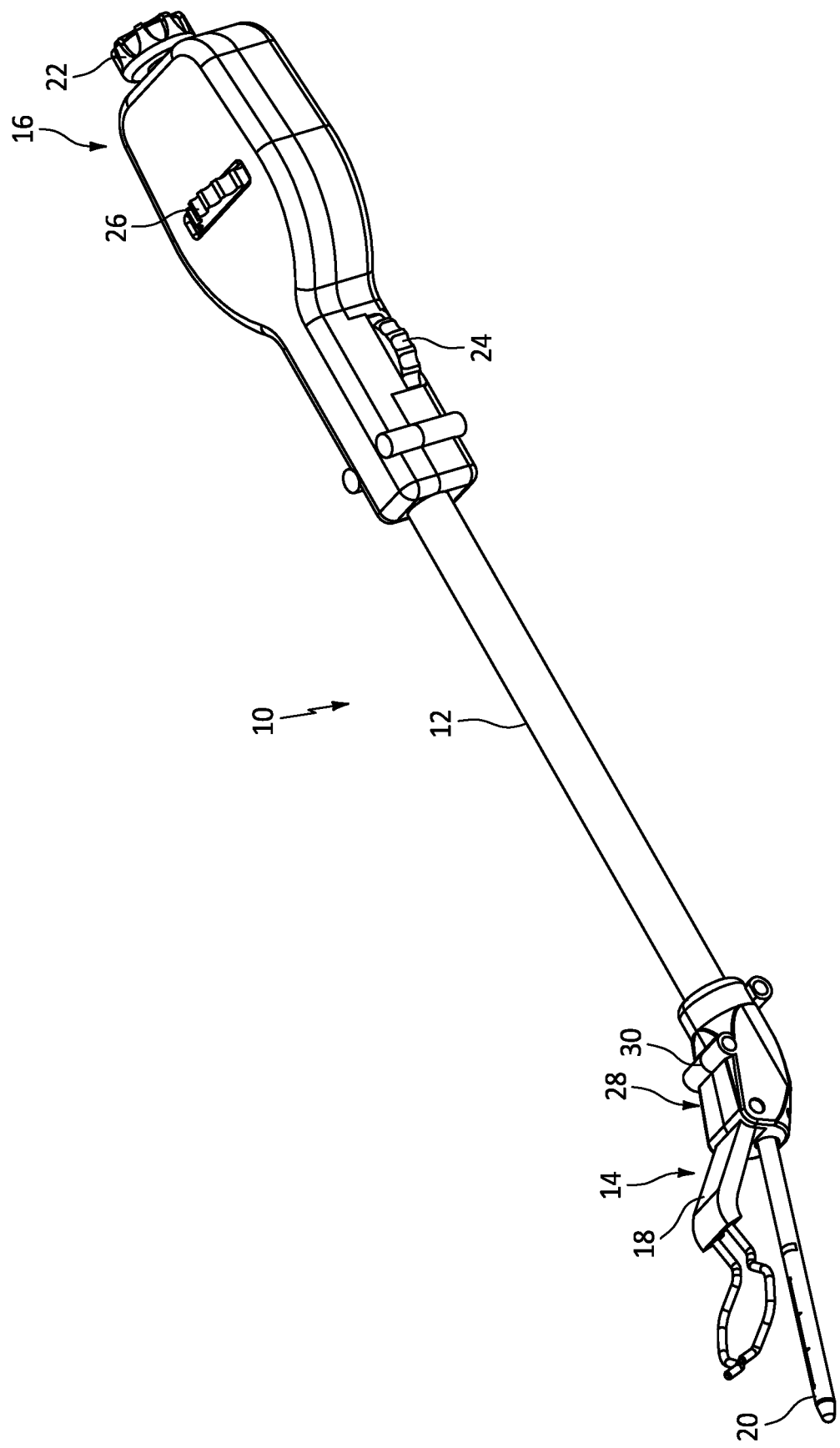
FIG. 2 is a perspective view similar to FIG. 1 with an upper jaw of the device in a lifted position.
Figure 3:
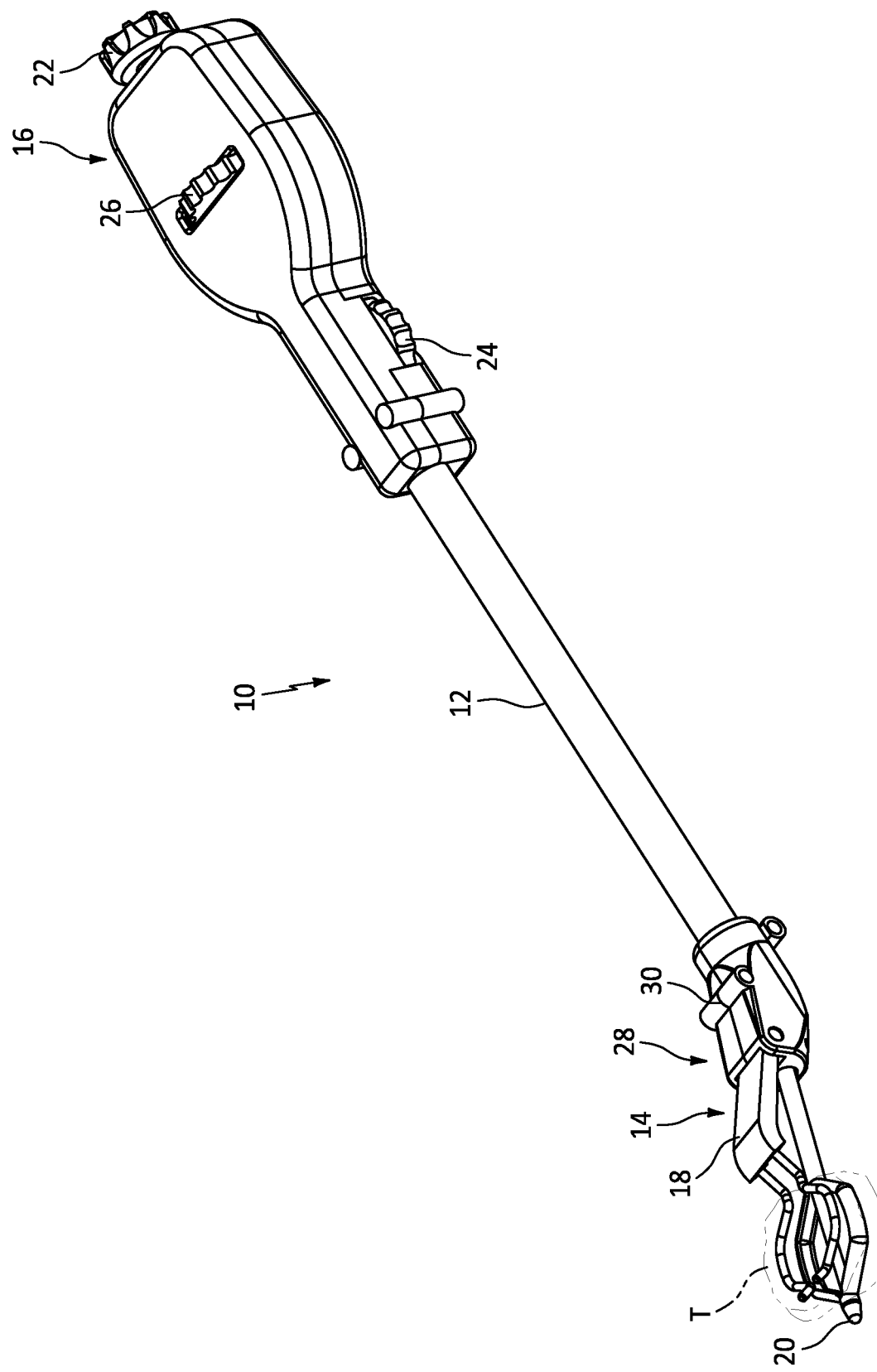
FIG. 3 is a perspective view similar to FIG. 1 with the upper and lower jaws of the device clamped onto a layer of tissue.

Jaw assembly 14 includes an upper jaw member 18 and a lower jaw member 20. As discussed in further detail below, upper jaw member 18 can be pivoted relative to lower jaw member 20 between an open position (FIG. 2) wherein upper jaw member 18 is lifted or pivoted away from lower jaw member 20, and a clamping position (FIG. 3) wherein upper jaw member 18 is lowered or pivoted toward lower jaw member 20. Also as will be further discussed below, upper jaw member 18 and lower jaw member 20 can be deployed around a site in a body part or tissue T, for example a blood vessel or vascular wall, to isolate that area and thereby facilitate surgical procedures at that site.

Control housing 16 has control units such as knob 22, wheel 24 and/or wheel 26 that can be manipulated by a user to cause the desired movements of upper and lower jaw members 18, 20. Knob 22 and/or 26, for example, can be rotated to cause upper jaw member 18 to pivot relative to lower jaw member 20, while wheel 24 can be rotated to cause lower jaw member 20 to move between a withdrawn position and an expanded position, all as will be discussed in detail below.

Elements of control housing 16 are connected to upper and lower jaw members 18, 20 through elongate shaft 12, for example with configurations of push or pull rods and tubes, to produce the desired movement when knobs and wheels 22, 24, 26 are, in this embodiment, manipulated by a user of the device. As will be further discussed herein, the controls can be operated robotically as well.

Because jaw assembly 14 is mounted at the distal end of shaft 12, jaw assembly can be deployed through a body wall to an internal location for performing the desired occlusion with a minimally sized incision, for example an incision of 1-2 inches, while still allowing the user a full range of control of the elements of the device, and sufficient space for deployment of additional tools or instruments for conducting the desired procedure.

FIG. 1 shows jaw assembly 14 with upper and lower jaws 18, 20 extending from a jaw housing assembly 28. As shown, jaw housing assembly 28 includes a jaw housing 30 that surrounds linkages or connections between control elements in shaft 12 and the jaw members 18, 20. FIG. 4 shows an internal view of one embodiment of jaw assembly 14, with a portion of jaw housing 30 removed. Upper jaw member 18 can be mounted in a lever 32 that can be pivotably mounted in jaw housing 30. Lever 32 and jaw housing 30 can be pivotably mounted by engaging structure on each element. For example, lever 32 can have laterally projecting posts 34 that engage in internal structure of jaw housing 30 (further described and illustrated below) and establish a pivot point around which lever 32 and upper jaw member 18 pivot when operated from control housing 16. Alternatively, posts could be positioned on the housing and engage with appropriate structure on the lever.

In this configuration, lever 32 also has a proximal head 36, in this case two laterally spaced plates, each defining a slot 38. A pull rod 40 is shown extending along shaft 12 (schematically illustrated in broken lines) to a linkage 42. Linkage 42 has posts 44 that slidably engage in slot 38 and a slot in jaw housing 30 which is further described below. Pull rod 40 can be actuated, for example caused to move axially relative to shaft 12, by operation of controls at control housing 16, for example by rotating knob 22. Axial movement of pull rod 40 is shown by the arrows 41 in FIGS. 4 and 5, and in this configuration, FIG. 5 shows pull rod 40 moved distally, which motion is transmitted to lever 32 through linkage 42 to cause a clockwise pivot of lever 32 around posts 34 to open the jaw assembly 14 by lifting upper jaw member 18 away from lower jaw member 20 as shown in FIG. 5.

FIGS. 6 and 7 further illustrate operation of lower jaw member 20, also with a portion of jaw housing 30 removed to illustrate internal components. In this configuration, lower jaw 20 can be a catheter tube having a central slit 46 leading up to but not reach a distal tip 48 of lower jaw 20. Distal tip 48 is connected within lower jaw 20 along a control rod 50 into a pull tube 52 that is also disposed along shaft 12. As indicated by the arrows in FIGS. 6 and 7, in this embodiment proximal movement of pull tube 52 pulls control rod 50 proximally, while lower jaw member 20 is fixed relative to jaw housing 30. This results in control rod 50 pulling distal tip 48 proximally, which results in lateral spreading of lower jaw member 20 by the portions 54 of lower jaw member 20 that are on either side of slit 46 moving laterally away from each other. Pull tube 52 is connected back through shaft 12 to control housing 16, where operation of a control member, for example wheel 24, moves pull tube 52 along axially along shaft 12 and thereby causes the desired movement of lower jaw 20 between the withdrawn position (FIG. 6) and the laterally expanded position (FIG. 7).

Figure 9:
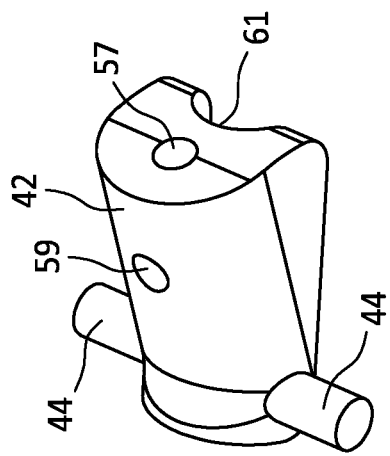
FIGS. 8-10 further illustrate housing and linkage components of this embodiment.
Figure 8:
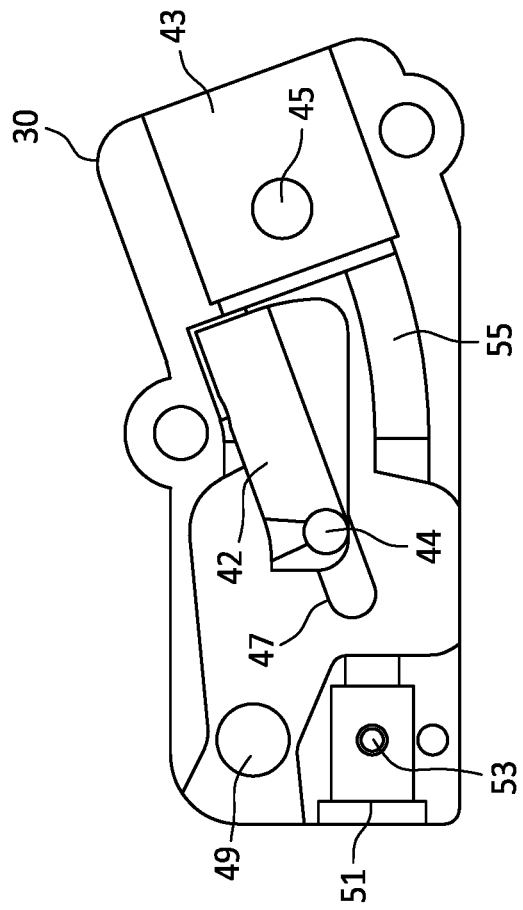
Figure 10:
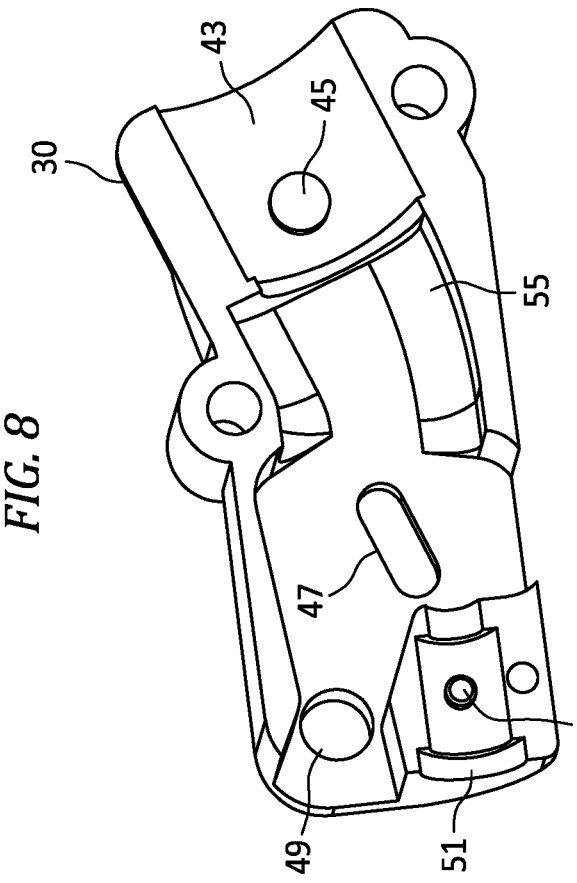

FIGS. 8-10 further illustrate features of housing 30 and linkage 42. FIG. 8 shows an internal view of housing 30. As is evident from the parting line seen in FIG. 1, housing 30 in this configuration is a two-part molded structure. This of course can be modified within the scope of the present disclosure. In the meantime, one side of the two-part structure of housing 30 is removed to show internal features of the other part, and these parts can be considered to be mirror images of each other. FIG. 8 shows linkage on position relative to housing 30, while FIG. 9 shows an isolated view of linkage 42, and FIG. 10 shows housing 30 from a different angle and with linkage 42 removed to better illustrate features within housing 30.

Starting at a proximal side of housing 30 (right side in FIG. 8), a shaft receiving area is shown at 43, and can have a structure, in this case an indentation 45, for engaging with the shaft 12 and/or a securing member passing through the shaft. A slot 47 is shown in housing 30 and slot 47 is shown as an internal groove, that is, in this configuration it does not pass through the sidewall of housing 30. Slot 47 receives post 44 of linkage 42 and allows linkage 42 to slide relative to housing 30 as desired. Of course, these structure can be reversed, that is, internally projecting structure can be provided on the housing, and a slot or groove on the external surface of the linkage, or other configurations as well could be utilized, to provide the slidable mounting of linkage 42 relative to housing 30.

At a distal side of housing 30 (left side in FIG. 8), an opening 49 is configured to receive posts 34 of lever 32 and thereby provide the desired pivotable mounting of lever 32 in housing 30. These structures also can be reversed, that is, with internal posts on housing 30 and openings or other receptacles on lever 32, either of which can be used to provide the desired pivotable mounting.

A jaw receiving area 51 is shown in housing 30, where lower jaw member 20 can be secured, for example using engaging structure with aperture 53 or in any other manner. Also, as mentioned above, in some embodiments a pull tube 52 (FIGS. 6 and 7) is attached to control rod 50 for controlling movement of lower jaw assembly 28. FIGS. 8 and 10 illustrate a contoured area 55 defined in a central portion of housing 30 for guiding pull tube 52, in this configuration in a slidable manner so that pull tube 52 can be used to move control rod 50 and thereby move the lower jaw between the positions of FIGS. 6 and 7.

FIG. 9 shows linkage 42 of this configuration. As shown, linkage 42 has an opening 57 for receiving an end of pull rod 40, as well as posts 44 for mounting within housing 30. Further, an opening 59 in an upper portion of linkage 42 can show an upwardly angled portion of pull rod 40 to allow visual confirmation of proper engaging of pull rod 40 within linkage 42. FIG. 9 also shows a curved area 61 at a lower portion of linkage 42. Curved area 61 can be sized to an outer contour of pull tube 52 so that these elements can slide relative to each other in a stable manner.

Figure 12:
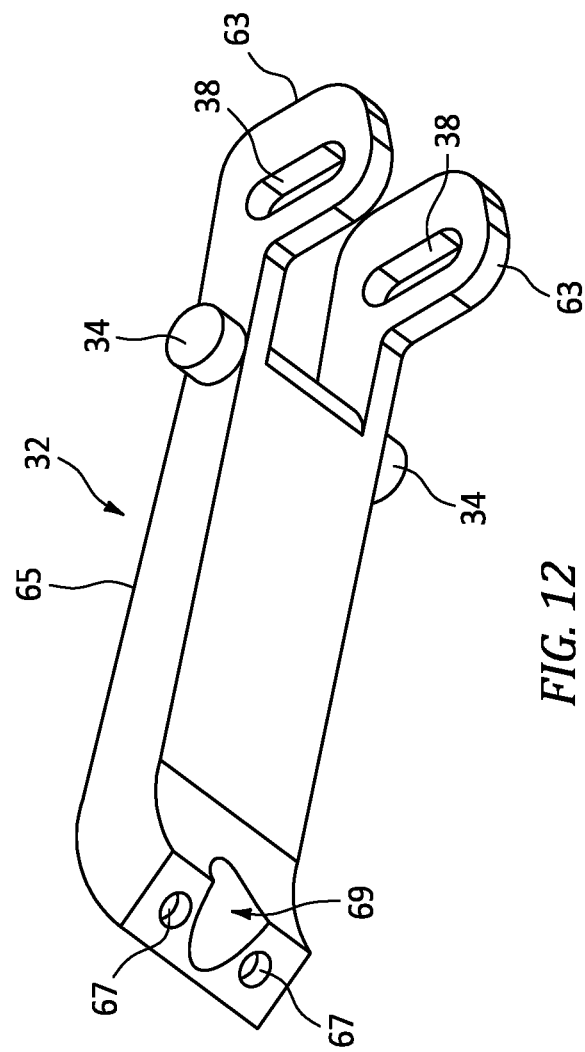
FIGS. 11-12 further illustrate features of a lever for an upper jaw member of this embodiment.
Figure 11:
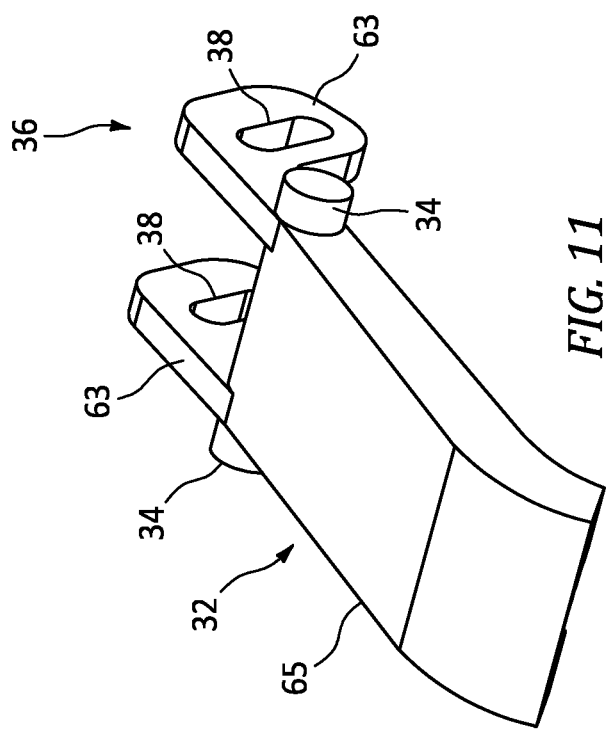

FIGS. 11 and 12 illustrate lever 32 of this embodiment to better show additional features thereof. As shown, lever 32 has proximal head 36 defined by two spaced proximal extensions 63, each having a slot 38 defined therein for receiving posts 44 of linkage 42. These proximal extensions 63 in this embodiment extend between linkage 42 and housing 30 such that posts 44 extend through slots 38 and into slot 47 of housing 30. Linkage 42 therefore is engaged at least partially between proximal extensions 63. The distal portion 65 of lever 32 defines a housing 65 for holding upper jaw member 18, specifically for receiving the wire form arms of the upper jaw member 18. The distal portion of housing 65 can be downwardly angled as shown to help properly position the upper jaw member 18 when pivoted to the closed position. Further, openings 67 are shown for receiving components of the upper jaw member 18, in this case wire form elements which are further discussed herein. A rounded cutout 69 can be provided on a lower surface of housing 65 to receive lower law member 20 when lever 32 is pivoted into the closed position. This again helps to provide a stable device, particularly when the jaw are closed on tissue during a surgical procedure.

Figure 14:
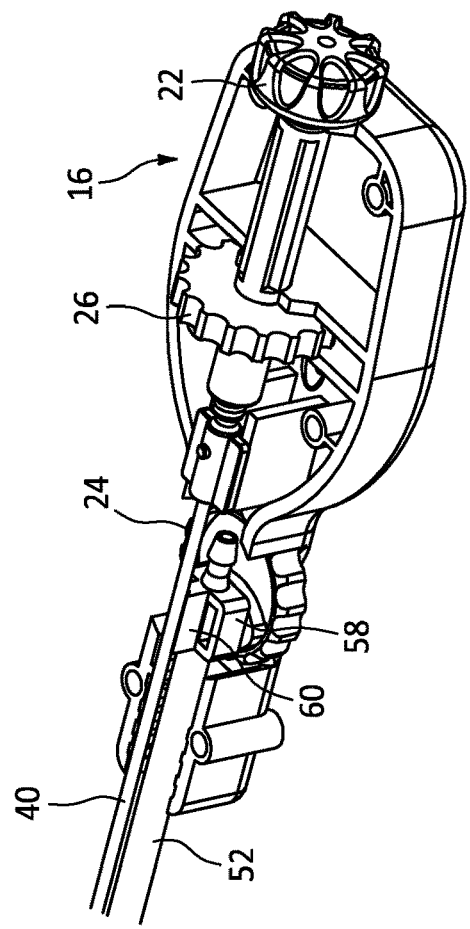
FIG. 14 is an internal view of the proximal control housing of the device of FIG. 1 showing a non-limiting configuration of a control for moving the lower jaw between the withdrawn position and the expanded position.
Figure 13:
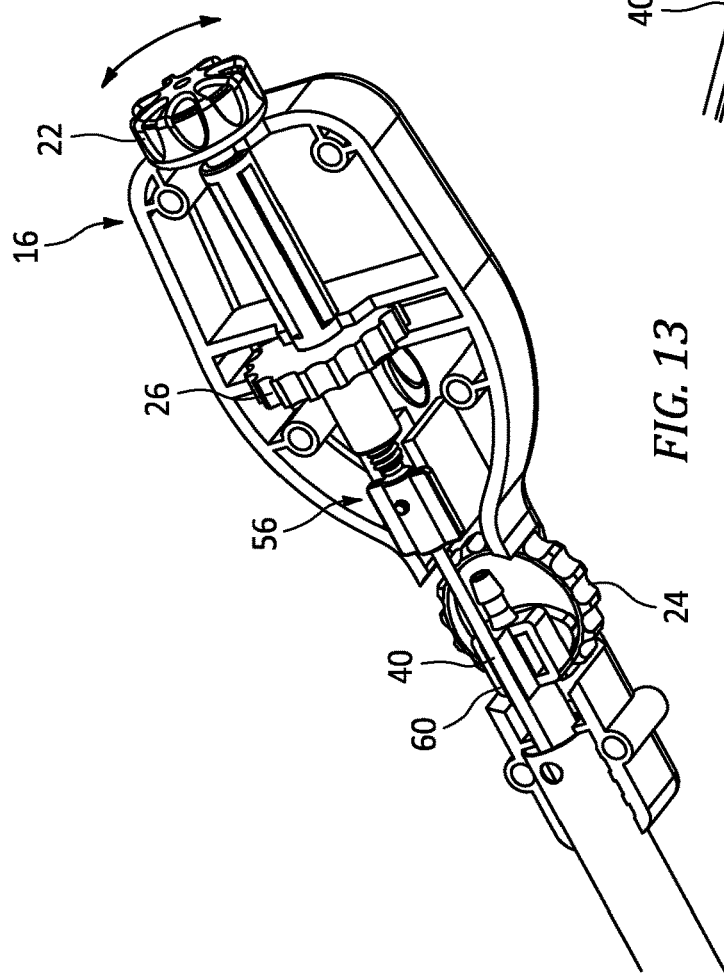
FIG. 13 is an internal view of the proximal control housing of the device of FIG. 1 showing a non-limiting configuration of a control for the upper jaw positioning.

FIGS. 13 and 14 show control housing 16 with a portion of the housing removed to illustrate internal components. As shown, pull rod 40 extends into housing 16 and into a threaded connection 56. On the other end of threaded connection, knob 22 and wheel 26 are positioned for use in manually rotating knob 22 or wheel 26 to cause the desired axial movement of pull rod 40 along shaft 12 and, thereby, the pivot of upper jaw 18 relative to lower jaw 20. These drawings also show pull tube 52 extending proximally out of shaft 12 and into engagement with a structure 58 mounted relative to wheel 24 such that rotation of wheel 24 relative to control housing 16 axially moves pull tube 52 relative to the fixed jaw housing. This movement is conveyed along pull tube 52 to control rod 50 (not shown in FIGS. 13 and 14) such that the movement causes movement of distal tip 48, and proximal movement of distal tip 48 spreads positions 54 of lower jaw member 20 as discussed above.

Numerous additional features are disclosed in the internal views of FIGS. 13 and 14. For example, pull rod 40 in this configuration is supported by a support member 60 that can, for example, be defined as an arcuate surface on structure 58 or in other configurations could be positioned elsewhere. Support member 60 helps to provide controlled and stable axial movement of pull rod 40 within shaft 12 when needed.

Figure 16:
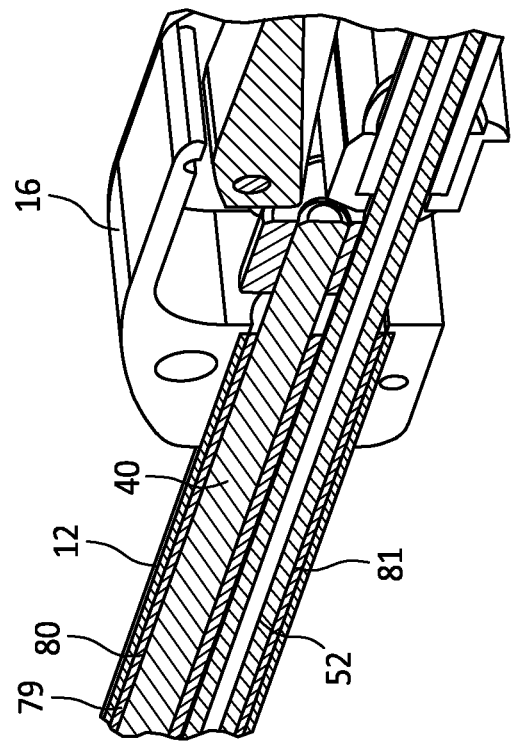
FIGS. 15-16 illustrate an alternate embodiment having a support member for internal components of the shaft.
Figure 15:
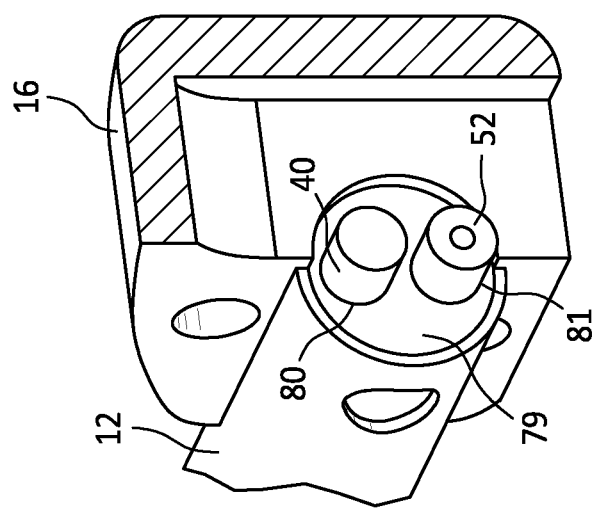

FIGS. 15 and 16 further illustrate another configuration which allows support within shaft 12, in this case in the form of a member 79 which can be separate extrusion with through-lumens 80, 81 to further support pull rod 40 and pull tube 52.

FIGS. 17 and 18 illustrate another non-limiting configuration wherein upper jaw member 18 is defined by two jaws 62, in this case shown as wire form jaw members. Jaws 62 are configured to be rotated around a longitudinal axis thereof, see axis A. This rotational movement allows jaws 62 to be rotated between a withdrawn position as illustrated in FIG. 17, to a laterally expanded position similar to the configuration of upper jaw 18 as shown in FIG. 1. In order to provide this rotation of jaws 62, jaws 62 can be connected to shafts 64, each of which can be mounted with a gear 66, which advantageously allows for rotation of jaws 62 as desired through rotation imparted through shaft 12 from control housing 16. It should be appreciated that since gears 66 are engaged with each other, driving of either gear will result in the counter directional rotation of both jaws 62 as desired.

Figure 19:
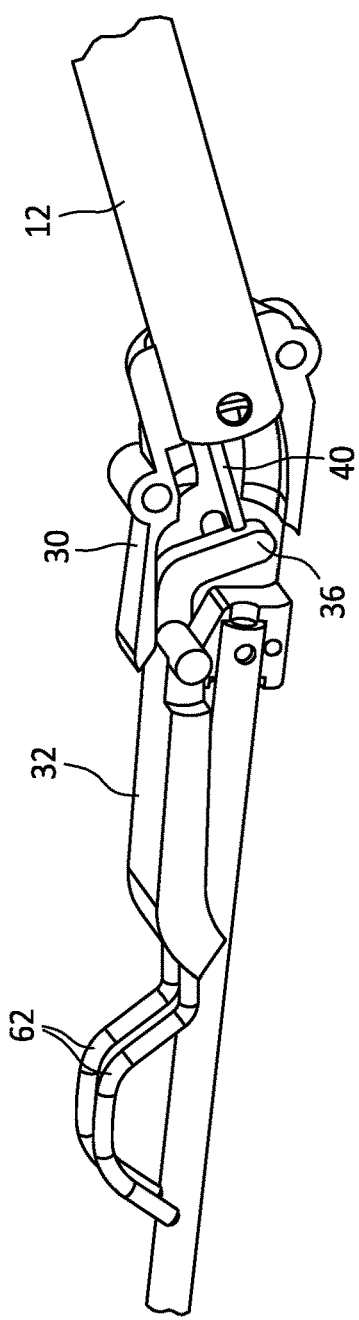
FIG. 19 is an internal view of an alternative and non-limiting configuration for driving pivoting the upper jaw assembly.
Figure 20:
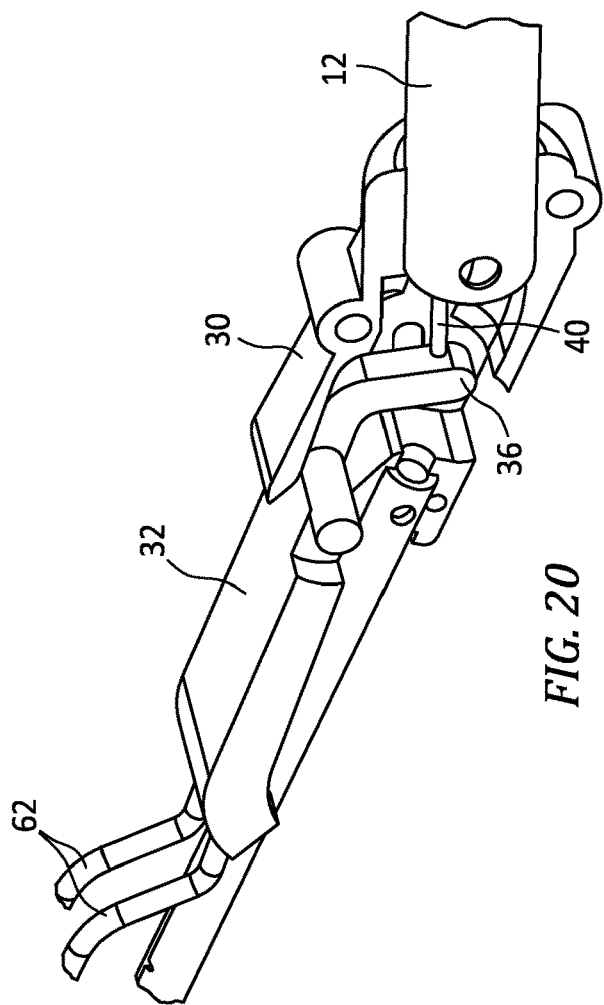
FIGS. 20-22 are enlarged and alternate views of the structure of FIG. 19.
Figure 21:
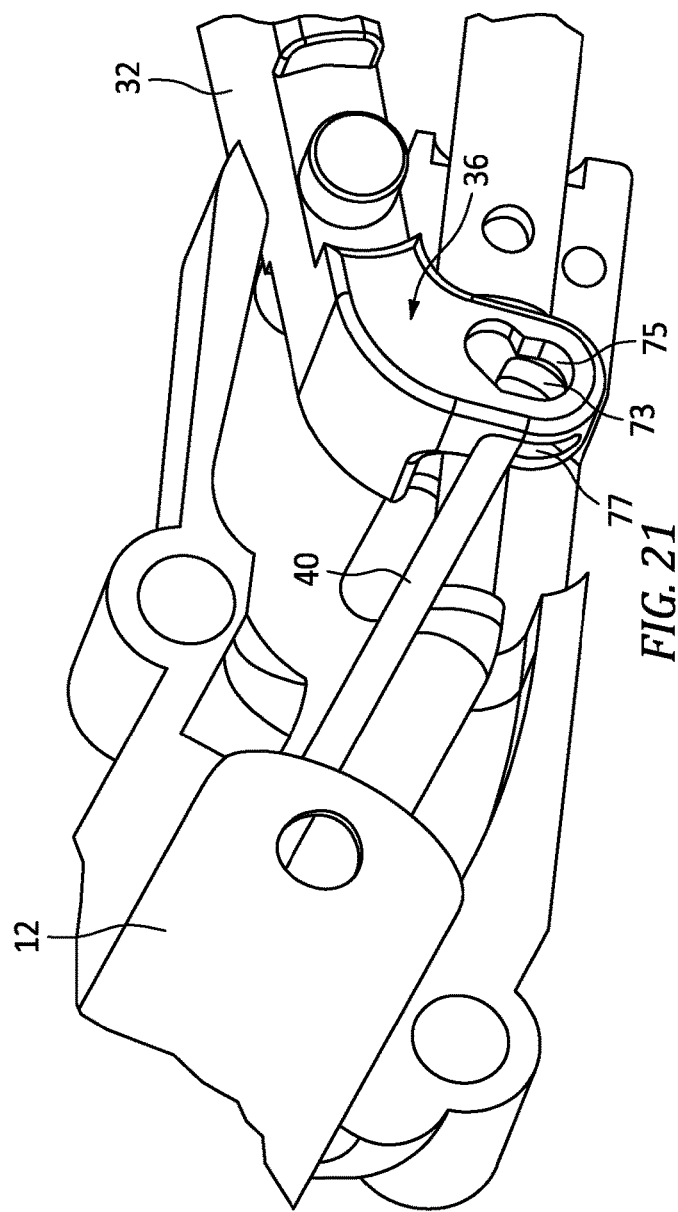
Figure 22:
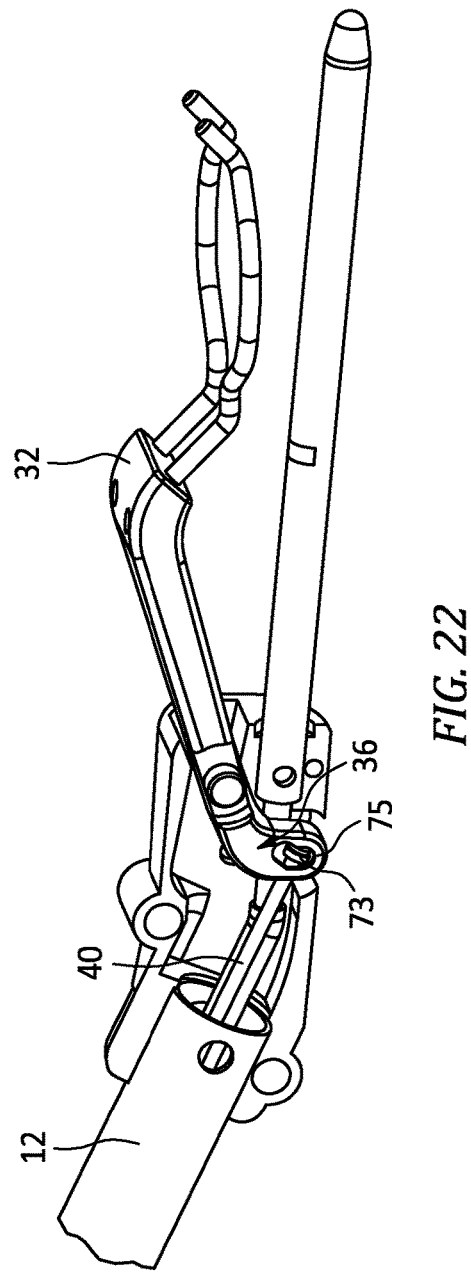

FIGS. 19-22 illustrate an alternate embodiment wherein pull rod 40 can be directly connected to lever 32 without a linkage. As shown, best in FIG. 21, in this embodiment, pull rod 40 can have head piece 73 in the shape of a knob or other enlarged portion, and proximal head 36 of lever 32 can define a slotted receptacle area 75 for pivotably receiving head piece 73. In this configuration, head piece 73 can be assembled within receptacle area 75, or otherwise disposed therein, and a slot 77 in proximal head 36 allows pull rod 40 to pivot relative to proximal head 36 and lever 32 during movement of pull rod 40. It should be appreciated that this configuration can allow for a simple and still reliable connection of components without the need for a linkage as is present in the earlier embodiment. Note that jaws 62 in FIGS. 19-20 are shown in a pivoted upward position for example as made possible by the embodiment of FIGS. 17 and 18. This is not required for the embodiment of FIGS. 19 and 20, which could be implemented regardless of whether jaws 62 are pivotable.

Figure 24:
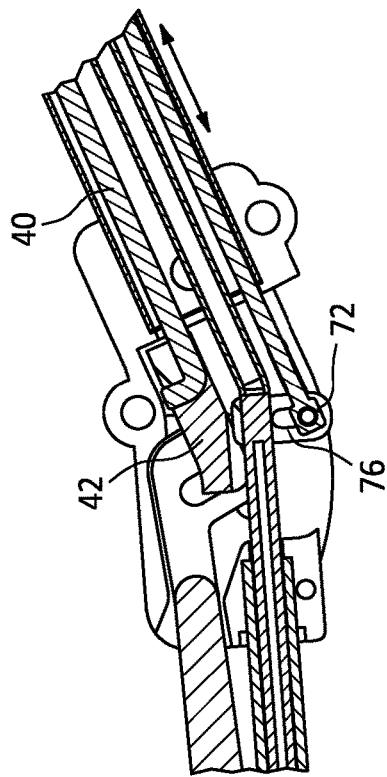
FIGS. 23-28 illustrate a further alternative and non-limiting control linkage the lower jaw member.
Figure 23:
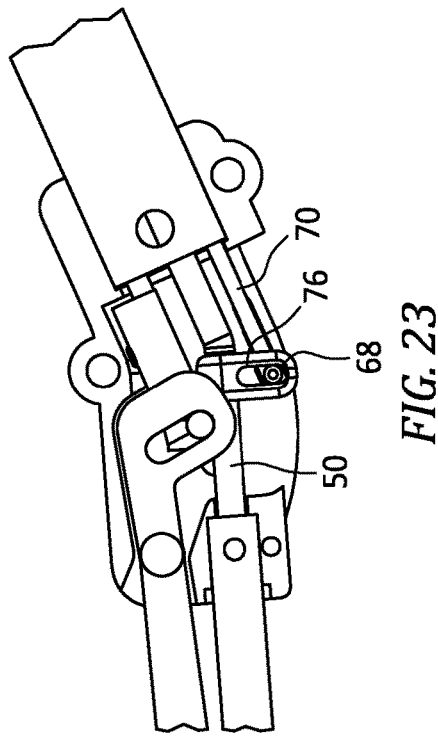
Figure 25:
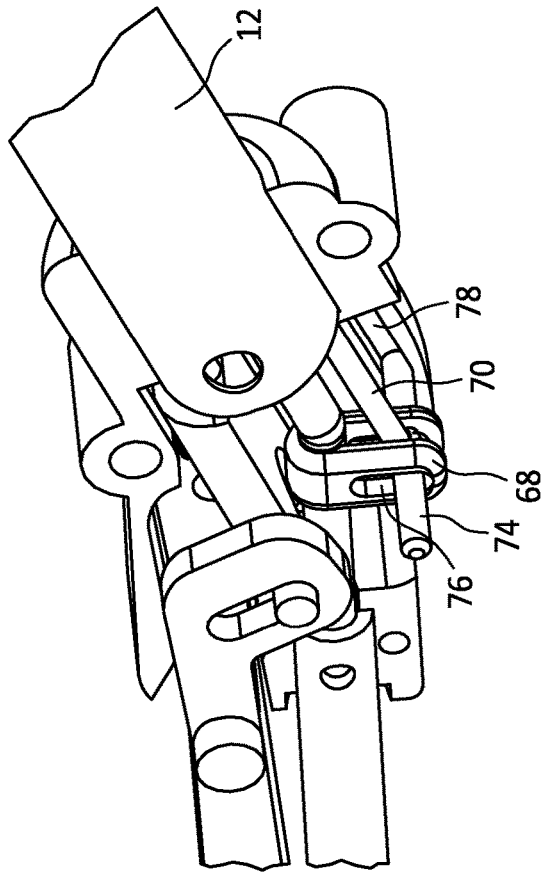

FIGS. 23-25 illustrate another embodiment wherein alternate structure is provided for operating the lower jaw member. As shown, control rod 50 is still slidable mounted within the lower jaw member 20. However, in this configuration control rod 50 is not moved or actuated by pull tube 52, but instead is connected through a yoke member 68 to an additional pull rod 70 that slidable extends through shaft 12 for control at control housing 16. In this configuration, yoke member 68 us a generally U-shaped body defining an inner space for receiving an end of pull tube 52, and also for receiving a pivotable connection to additional pull rod 70. The pivotable connection can be defined by a distal head 72 on rod 70 connected to a horizontal shaft 74. Shaft 74 can be slidable mounted within a slot 76 also defined in yoke member 68 such that rod 70 and/or shaft 74 can both pivot relative to yoke member 68, and can move vertically relative to yoke member 68 by traversing slot 76. For further stability, shaft 74 can also ride along grooves 78 that can be defined in housing 30 as best seen in FIG. 25.

In this configuration, although pull tube 52 remains for the useful function of defining a passage back to the proximal end of the device where the effectiveness of hemostasis can be monitored for leakage so the user can see if there is a good seal before creating an aortotomy, otherwise pull tube 52 is not used for actuating the device, and thus in this configuration serves primarily as a tube, but not a pull tube.

Figure 26:
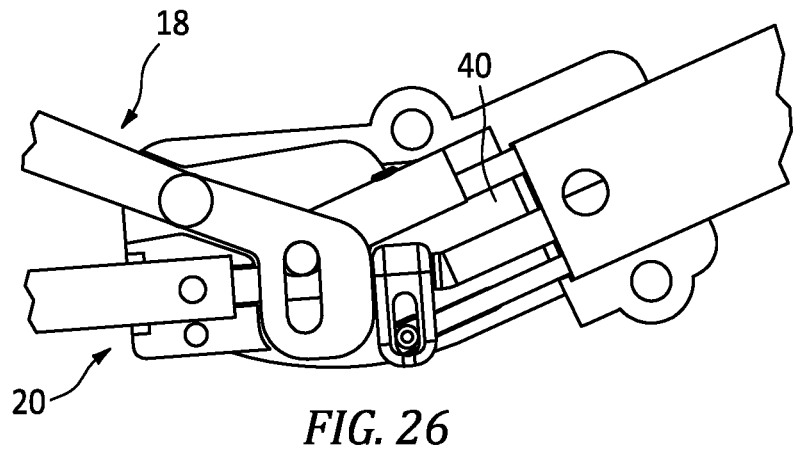
Figure 27:
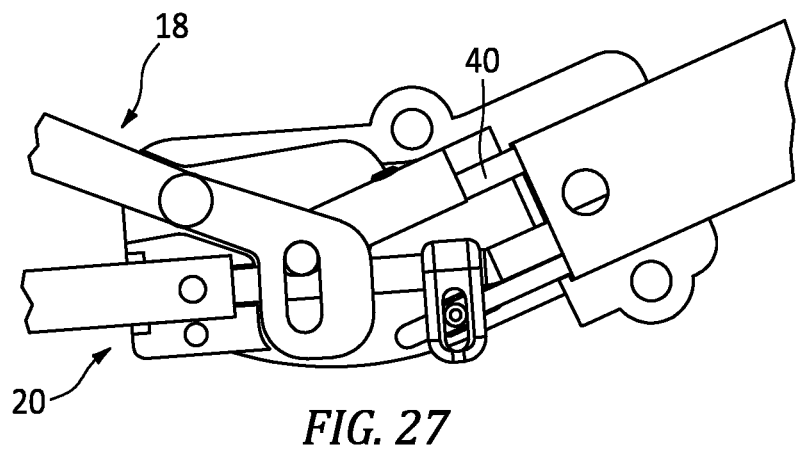
Figure 28:
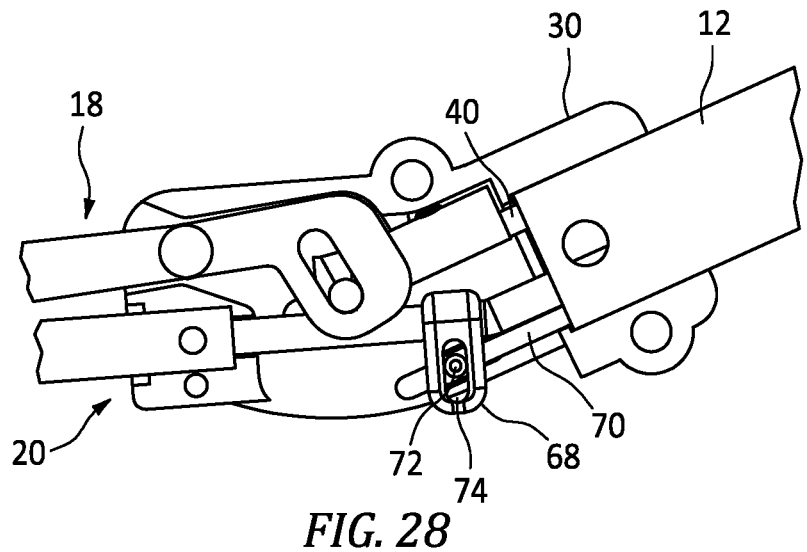

When additional control rod 70 is moved axially along shaft 12 in a proximal direction, shaft 74 moves proximally along with rod 70, and also pulls yoke 68 along slot 78, with shaft 74 moving upward in slot 76 during this movement. Yoke 68 connected to control rod 50 pulls distal tip 48 of the lower jaw member 20 proximally and causes the lower jaw to move to the expanded position as discussed above. FIGS. 26-28 sequentially illustrate this movement from a distal position in FIG. 26 where the lower jaw member is withdrawn to a proximal position as shown in FIG. 27 where the lower jaw would be expanded. FIG. 28 then illustrates the next step of a method using this device, wherein the upper jaw is now closed by proximal movement of pull rod 40 to pivot the upper jaw member 18 toward the lower jaw member 20 and the closed position.

Referring specifically to FIG. 24, this view is a cross sectional view and further illustrates an aspect of the device that is mentioned above, specifically the connection of pull rod 40 to linkage 42, which in this embodiment is accomplished by forming a bend in the distal end of pull rod 40 and capturing this bend within linkage 42 as shown. Of course, other methods for connecting pull rod 40 to linkage 42 could be utilized within the broad scope of this disclosure.

It should be appreciated that jaw assembly 14 is shown in FIG. 1 as being angled relative to shaft 12. Specifically, the illustrated embodiment has jaw assembly 14 in a non-straight extension from jaw housing assembly 28. It should be appreciated that in some configurations, it may be preferable to have jaw assembly 14 extend in a straight configuration from shaft 12. Thus, the angle of jaw assembly 14 relative to shaft can be between 0 and 60 degrees, and in some configurations between 0 and 45 degrees. In one configuration, the angle can be between 0 and 30 degrees, while in still another non-limiting configuration, the angle is substantially 0 degrees, and the jaw assembly is substantially straight relative to shaft 12.

In use, device 10 can be employed to occlude a desired occlusion zone in preparation for a surgical procedure as follows:

In use, the apparatus of the present disclosure can be inserted through a 2-3 inch incision and share space with other instruments, for example other instruments intended to conduct the desired surgical procedure once the device of the present disclosure is deployed. Alternatively, the occlusion device could be deployed through a large cannula, for example a 13-15 mm cannula, or in any other ways suitable to a procedure wherein the presently disclosed device can be usefully deployed.

In one method of use, the device of the present disclosure can be used to establish hemostasis around an area of an aorta to establish a blood free zone which can then be focused on in further procedures. One such procedure involves sewing of a vein or arterial graft to the aorta for revascularization of diseased or otherwise compromised coronary arteries. The device of this disclosure prepares an area of the aorta for this process. The method can start by accessing the aorta with the occlusion device and positioning the occlusion device such that the body part, in this case a portion of the aorta, is between the lower jaw and the upper jaw. This can be accomplished by mapping an area of the aorta to be worked upon, and making a small incision for the lower jaw in an area such that when inserted through the incision, the jaw extends beneath the area to be occluded. Once in the desired location, by operating the control member, the user can configure the lower jaw to the expanded position, and then cause the upper jaw to pivot toward the lower jaw and occlude the body part between the lower jaw and the upper jaw. Note that a membrane, not discussed above, can be disposed between the expanded portions of the lower jaw, and this membrane along with the clamping of the jaws creates the desired hemostasis as with prior devices. Thus, once deployed in this manner, with no leakage showing through the pull tube, the surgeon or used is then ready to proceed with the desired grafting or the like.

When the procedure is completed, the occlusion device can be removed by reversing the steps outlined above.

As mentioned above, the device of the present disclosure can be deployed through a small incision, or if preferable under specific circumstances, the device can be deployed through a large sized cannula.

Referring back to FIG. 1, in another configuration, the device as disclosed herein can be provide with a shaft 12 such that once hemostasis is established as desired, the shaft 12 with control housing 16 can be pivoted out of the way to allow better accessibility and visibility for the surgeon. This can be accomplished by making shaft 12 from flexible materials or structures, and use of pull rods and the like through shaft 12 that are themselves flexible. This can be accomplished through any manner known to persons of ordinary skill in the art. The described flexibility is schematically represented by arrows A in FIG. 1.

Figure 29:
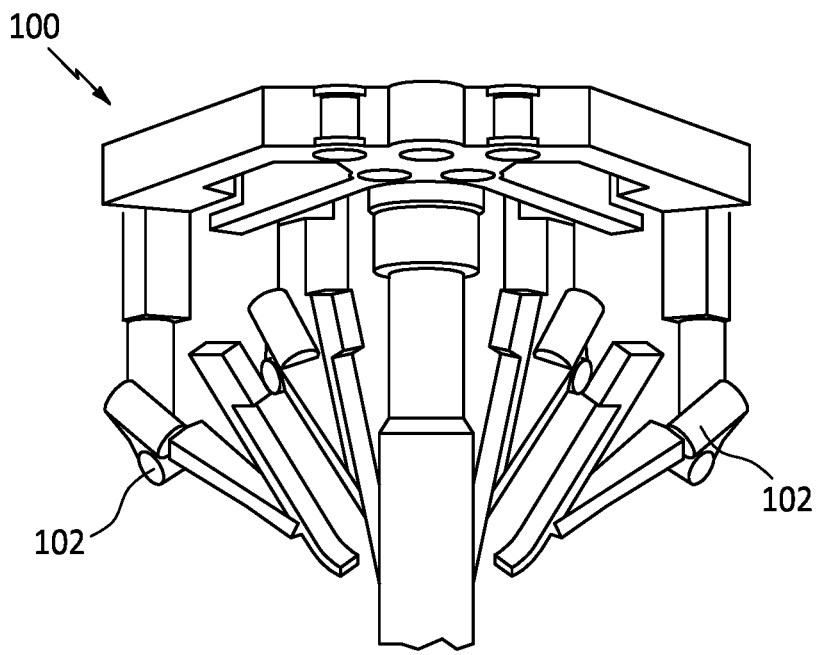
FIGS. 29-30 illustrate aspects of a robot mechanism-controlled embodiment.
Figure 30:
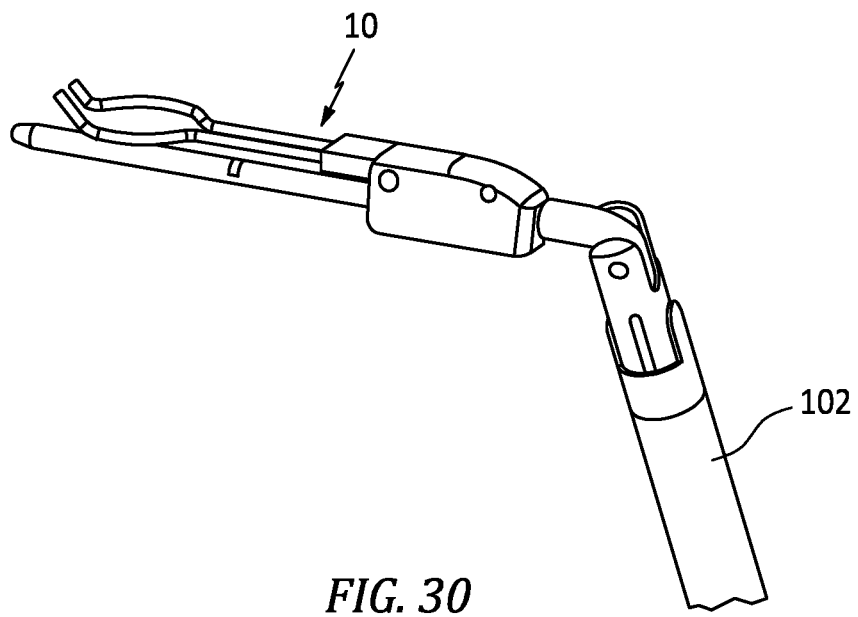

In a further configuration, the device of the present disclosure can be deployed and operated by a robot or other mechanically automated method. FIGS. 29 and 30 illustrate such a configuration. FIG. 29 shows a typical robotically controlled mechanism 100 wherein a plurality of arms 102 are controlled by programming or a remote user to perform various routines. One or more such arms 102 can be equipped with a device 10 as disclosed herein, with a controller having suitable programming to issue commands to the control mechanisms within device 10 to both position and operate the device as needed. Of course, other arms 102 could then be deployed with additional tools or devices for conducting the desired procedure.

Although particular steps and sequences are shown, described, and claimed, it should be appreciated that steps may be performed in any order, separated or combined unless otherwise indicated, and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be appreciated that within the scope of the appended claims, the disclosure may be practiced other than as specifically described. Thus, the scope of the present claims is not specifically limited by the details of specific embodiment disclosed herein, but rather the claims define the full and reasonable scope of the invention.

I claim:

1. An occlusion device, comprising:
   an elongate shaft;
   a lower jaw extending from a distal end of the elongate shaft;
   an upper jaw pivotably mounted at the distal end of the shaft and pivotable relative to the lower jaw; and
   a control member at a proximal end of the elongate shaft, the control member being operatively associated with the upper jaw to cause pivot of the upper jaw relative to the lower jaw;
   a housing at the distal end of the shaft, wherein the upper jaw is pivotably mounted to the housing; and
   a linkage movable relative to the housing and connected to the upper jaw, and a pull rod axially movable along the elongate shaft and connected to the linkage, whereby axial movement of the pull rod moves the linkage and causes pivot of the upper jaw relative to the lower jaw;
   wherein the upper jaw is mounted in a lever pivotably mounted to the housing at a point of the lever, and having a proximal head that is connected to the linkage.

2. The device of claim 1, wherein the lower jaw is laterally configurable between a withdrawn position and an expanded position, and wherein the upper jaw comprises a clamping member corresponding in shape to the lower jaw when the lower jaw is in the laterally expanded position.

3. The device of claim 2, wherein the upper jaw is laterally configurable between a withdrawn position and an expanded position, and wherein the expanded position of the upper jaw corresponds in shape to the expanded position of the lower jaw.

4. The device of claim 3, wherein the upper jaw comprises at least two components, and the at least two components move between the withdrawn position and the expanded position by rotating around a longitudinal axis of the upper jaw.

5. The device of claim 4, wherein the at least two components have gears at proximal ends, and further comprising a rotation imparting member extending through the elongated shaft and rotatable from a proximal end of the elongated shaft to control position of the upper jaw between the withdrawn position and the expanded position.

6. An occlusion device, comprising:
   an elongate shaft;
   a lower jaw extending from a distal end of the elongate shaft;

an upper jaw pivotably mounted at the distal end of the shaft and pivotable relative to the lower jaw; and a control member at a proximal end of the elongate shaft, the control member being operatively associated with the upper jaw to cause pivot of the upper jaw relative to the lower jaw;

a housing at the distal end of the shaft, wherein the upper jaw is pivotably mounted to the housing;

a linkage movable relative to the housing and connected to the upper jaw, and a pull rod axially movable along the elongate shaft and connected to the linkage, whereby axial movement of the pull rod moves the linkage and causes pivot of the upper jaw relative to the lower jaw; and a pull tube mounted in the elongate shaft and extending into the housing for operating the lower jaw, wherein the linkage slides along the pull tube when the linkage is moved within the housing.

7. The device of claim 1, wherein the proximal head is angled relative to the body of the lever and has a slot, and wherein the linkage has a post slidably engaged in the slot.

8. The device of claim 1, wherein a pull rod is axially movable along the elongate shaft and pivotably connected to the upper jaw whereby axial movement of the pull rod causes pivot of the upper jaw relative to the lower jaw.

9. An occlusion device, comprising:

an elongate shaft;

a lower jaw extending from a distal end of the elongate shaft;

an upper jaw pivotably mounted relative to the lower jaw; and a control member at a proximal end of the elongate shaft, the control member being operatively associated with the upper jaw to cause pivot of the upper jaw relative to the lower jaw, further comprising a housing at the distal end of the shaft, wherein the upper jaw is pivotably mounted to the housing, wherein a pull rod is axially movable along the elongate shaft and pivotably connected to the upper jaw whereby axial movement of the pull rod causes pivot of the upper jaw relative to the lower jaw, and wherein the upper jaw comprises a lever mounted for pivot relative to the housing, and having a receptacle for pivotably receiving a distal head of the pull rod.

10. The device of claim 9, wherein the receptacle has a proximally facing slot, and the pull rod passes through the proximally facing slot.

11. The device of claim 1, wherein the lower jaw comprises a flexible member having an axial slit, and further comprising a control rod slidable in the lower jaw and connected to a distal end of the lower jaw whereby proximal movement of the control rod pulls the distal end of the lower jaw proximally and moves the lower jaw to an expanded position.

12. The device of claim 11, further comprising a pull tube slidably mounted in the elongate shaft and connected to the control rod for controlling the lower jaw.

13. The device of claim 1, wherein the lower jaw extends from the elongate shaft at an angle relative to the shaft of between 0 and 60 degrees.

14. The device of claim 13, wherein the angle is between 0 and 45 degrees.

15. The device of claim 14, wherein the angle is between 0 and 30 degrees.

16. The device of claim 1, wherein the shaft is flexible.

17. The device of claim 1, further comprising a robot mechanism connected to the device and programmed to operate the control member.

18. A method for occlusion of a body part, comprising the steps of:

accessing the body part with an occlusion device, comprising an elongate shaft; a lower jaw extending from a distal end of the elongate shaft; an upper jaw pivotably mounted at the distal end of the elongate shaft and pivotable relative to the lower jaw; and a control member at a proximal end of the elongate shaft, the control member being operatively associated with the upper jaw to cause pivot of the upper jaw relative to the lower jaw; a housing at the distal end of the shaft, wherein the upper jaw is pivotably mounted to the housing, wherein a pull rod is axially movable along the elongate shaft and pivotably connected to the upper jaw whereby axial movement of the pull rod causes pivot of the upper jaw relative to the lower jaw, and wherein the upper jaw comprises a lever mounted for pivot relative to the housing, and having a receptacle for pivotably receiving a distal head of the pull rod;

positioning the occlusion device such that the body part is between the lower jaw and the upper jaw; and operating the control member to cause the upper jaw to pivot toward the lower jaw and occlude the body part between the lower jaw and the upper jaw.

19. The method of claim 18, wherein the lower jaw is laterally configurable between a withdrawn position and an expanded position, and wherein the upper jaw comprises a clamping member corresponding in shape to the lower jaw when the lower jaw is in the laterally expanded position; and further comprising the step of configuring the lower jaw to the withdrawn position during the accessing step, and configuring the lower jaw to the expanded position before the operating step.

20. The method of claim 18, wherein the upper jaw is laterally configurable between a withdrawn position and an expanded position, and wherein the expanded position of the upper jaw corresponds in shape to the expanded position of the lower jaw, and further comprising the steps of configuring the upper jaw to the withdrawn position before during the accessing step, and configuring the upper jaw to the expanded position before the operating step.

21. The method of claim 18, wherein the body part is a body part of a human aorta.

22. The method of claim 18, wherein the accessing step comprises entering the body through the abdominal wall and passing the lower jaw through the body part to an occlusion site on the body part.

23. The method of claim 18, further comprising the step of, after occluding the body part, pivoting the shaft to a pivoted position.

24. The method of claim 18, wherein the method is at least partially conducted by a robot mechanism.

* * * * *